United States Patent [19]

Adolphi et al.

[11] 4,213,992

[45] Jul. 22, 1980

[54] INSECTICIDAL CARBAMATES

[75] Inventors: Heinrich Adolphi, Limburgerhof; Annegrit Baumann, Mannheim; Rolf Huber, Ludwigshafen; Karl Kiehs, Lampertheim; Franz Merger, Frankenthal, all of Fed. Rep. of Germany

[73] Assignee: BASF Aktiengesellschaft, Fed. Rep. of Germany

[21] Appl. No.: 926,405

[22] Filed: Jul. 20, 1978

Related U.S. Application Data

[63] Continuation of Ser. No. 807,065, Jun. 16, 1977, abandoned.

[30] Foreign Application Priority Data

Jul. 9, 1976 [DE] Fed. Rep. of Germany ....... 2630912

[51] Int. Cl.$^2$ .................. A61K 31/415; C07D 231/34
[52] U.S. Cl. .............................. 424/273 P; 548/365; 548/364; 546/211; 424/267
[58] Field of Search ..................... 548/365; 424/273 P

[56] References Cited

U.S. PATENT DOCUMENTS 3,810,911  5/1974  Hoffmann et al. ................... 548/365

FOREIGN PATENT DOCUMENTS 681376 10/1952 United Kingdom ..................... 548/365

OTHER PUBLICATIONS

Chem. Abst., 1972, vol. 76, p. 677g.
Ebnöther et al., Helv. Chim. Acta, 1959, vol. 42, pp. 2013–2035.

*Primary Examiner*—Alan L. Rotman
*Assistant Examiner*—Natalia Harkaway
*Attorney, Agent, or Firm*—Keil & Witherspoon

[57] ABSTRACT

New carbamates, a process for their manufacture by reaction of salts of pyrazolinediones with a carbamyl halide, and pesticides containing these new carbamates as active ingredients.

The new carbamates may be used as insecticides and acaricides. They have an excellent action on sucking insects, especially aphids.

4 Claims, No Drawings

INSECTICIDAL CARBAMATES

This is a continuation of application Ser. No. 807,065 filed June 16, 1977, now abandoned.

The present invention relates to new carbamates, a process for the manufacture, and pesticides containing these carbamates as active ingredients.

The carbamates of the invention are compounds of the formula

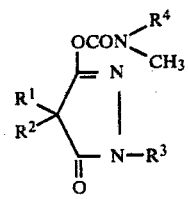

I, where $R^1$ and $R^2$ are identical or different and each denotes linear or branched alkyl of a maximum of 4 carbon atoms or unsubstituted or mono- or polysubstituted phenyl, $R^3$ denotes linear or branched alkyl of a maximum of 6 carbon atoms which is optionally substituted by phenyl, alkoxy, alkylamino or dialkylamino, $R^3$ further denotes cycloalkyl of 3 to 6 carbon atoms, unsubstituted phenyl, phenyl bearing one or several substituents selected from the group consisting of halogen, alkyl and alkoxy; N-alkylpyrrolidone or N-alkylpiperidine, $R^4$ denotes methyl or methoxy, and $R^1$ and $R^2$, together with the carbon atom whose substituents they are, may form a 5- to 7-membered ring.

Linear or branched alkyls for $R^1$ and $R^2$ in formula I are methyl, ethyl, propyl, isopropyl and butyl. Linear or branched alkyls for $R_3$ are methyl, ethyl, propyl, isopropyl, butyl, pentyl and hexyl, all of which may be substituted by phenyl, alkoxy, e.g., methoxy, alkylamino or dialkylamino, e.g., dimethylamino. Examples are the radicals 1-phenylethyl, 1-methyl-2-phenylethyl and 1-methoxyethyl. The phenyl radical which $R^1$, $R^2$ and $R^3$ may denote may bear halogen, e.g. chlorine or bromine, alkyl or alkoxy as substituents.

Depending on the substituents, the new carbamtes are yellowish oils or colorless solids exhibiting a strong biological action which permits their use as insecticides or acaricides for combatting animal pests. The compounds have an excellent action on sucking insects, especially aphids.

The new carbamtes may be obtained by reaction of salts of pyrazolinediones of the formula II with carbamyl halides of the formula III:

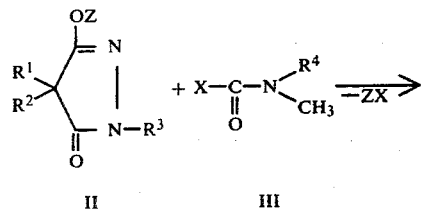

II    III

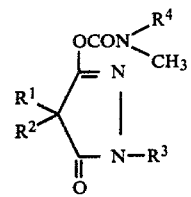

I $R^1$, $R^2$, $R^3$ and $R^4$ have the above meanings, Z denotes a cation and X halogen.

Suitable cations are alkali metal and alkaline earth metal ions, especially sodium, potassium and calcium; chlorine and bromine, especially chlorine, are suitable as halogen.

The reaction is carried out in solvents or diluents inert to the reactants; suitable examples are ethers such as diethyl ether, diisopropyl ether, tetrahydrofuran, dioxane and diglycol dimethyl ether; ketones such as acetone, methyl ethyl ketone and diisopropyl ketone; chlorinated aliphatic hydrocarbons such as dichloromethane, trichloromethane, carbon tetrachloride, 1,1-dichloroethane and 1,2-dichloroethane; aromatic hydrocarbon such as toluene, xylenes and chlorobenzenes; dimethylformamide; nitromethane; and nitriles such as acetonitrile and propionitrile.

In the reaction according to the invention, there are obtained, depending on the solvent, carbamates which may be contaminated by up to 25 wt% with the isomeric ureas of the formula

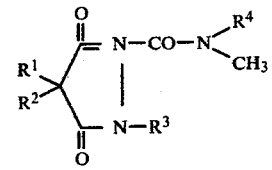

which are biologically less effective. In view of the high purity requirements placed on crop protection agents, this side reaction is extremely undesirable. It can be suppressed almost completely if an inert solvent of suitable polarity is used. e.g., acetone, tetrahydrofuran, diglycol dimethyl ether, toluene and chlorobenzene.

The starting materials are usually used in equimolar amounts. An excess of one or the other reaction component offers no great advantages.

The reaction temperature may be varied with a wide range. Generally, the temperature ranges from 15° to 100°, preferably from 30° to 90° C., unless the boiling point of the diluent sets an upper limit on the temperature.

The salts of pyrazolinediones used as starting compounds may be prepared by known methods (Helv. Chim. acta, 36, 74 et seq., 1953) by reaction of disubstituted malonic acid dialkyl esters of the formula IV with monosubstituted hydrazines of the formula V in the presence of suitable condensing agents, e.g., sodium methylate, in accordance with the following equation:

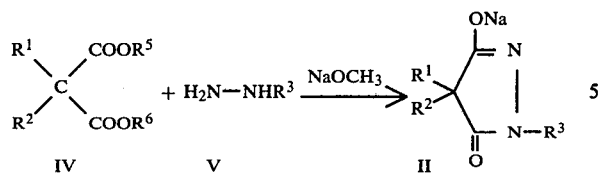

$R^1$, $R^2$ and $R^3$ have the above meanings, and $R^5$ and $R^6$ denote lower alkyl.

The salts of the pyrazolinediones can be prepared by this process in good yields and high purity. The salts are isolated in the following manner.

After the NaOCH$_3$ has been added, the CH$_3$OH which has formed is distilled off while continuously adding inert solvents, e.g., toluene, xylene, cumene, chlorobenzene and cyclohexane, until pure inert solvent distils off. The crystalline salt obtained is separated from the solvent and dried.

The pyrazolinedione salts prepared in this manner, especially the sodium salt, may be used without further purification for the synthesis of the carbamates.

The disubstituted malonic acid dialkyl esters required for the synthesis of the pyrazolinedione salts are known.

The preparation of the new carbamates is illustrated by the following examples.

(1a) 1-methyl-4-methyl-4-n-propyl-3-dimethylcarbamoyloxy-pyrazolin-(5)-one

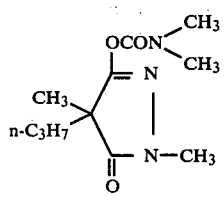

0.1 mole of dimethyl methyl-n-propylmalonate and 0.105 mole of methylhydrazine are placed in a flask. At room temperature, 0.1 mole of sodium methylate solution is dripped in and the reaction mixture is briefly stirred.

While continuously adding xylene, the methanol is distilled off until pure xylene passes into the receiver. The sodium salt of 2-methyl-4-methyl-4-n-propyl-pyrazolinedione is suction filtered, washed with ether and dried in vacuo at 40° C. The dry salt is suspended in 200 ml of absolute acetonitrile; at room temperature, dimethylcarbamoyl chloride is added. After refluxing for from 3 to 4 hours, the solution is concentrated at subatmospheric pressure, and the residue is taken up with ether and washed successively with water, sodium bicarbonate solution and again with water. After drying, the ether is distilled off. For approximately 30 minutes, solvents and impurities are removed at 70° C. and at subatmospheric pressure.

The yellow oil which remains is analytically pure. $n_D^{25}$: 1.4768; yield: 80%.

|  | C | H | O | N |
|---|---|---|---|---|
| Calc.: | 54.8 | 7.9 | 19.9 | 17.4 |
| Found: | 54.4 | 8.1 | 20.5 | 17.0 |

(1b) 2-methyl-4-methyl-4-n-propyl-5-dimethylcarbamoyloxypyrazolin-(3)-one

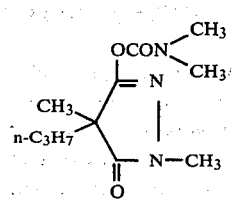

The sodium salt of 2-methyl-4-methyl-4-n-propyl-pyrazolinedione prepared and isolated as in Example 1 is suspended in 200 ml of absolute tetrahydrofuran; at room temperature, dimethylcarbamoyl chloride is added. After refluxing for from 3 to 4 hours, the solution is concentrated at subatmospheric pressure, and the residue is taken up with ether and washed successively with water, sodium bicarbonate solution and again with water. After drying, the ether is distilled off. For approximately 30 minutes, solvents and impurities are removed at 70° C. and at subatmospheric pressure.

The yellow oil which remains is analytically pure. $n_D^{25}$: 1.4680; yield: 80%

|  | C | H | O | N |
|---|---|---|---|---|
| Calc.: | 54.8 | 7.9 | 19.9 | 17.4 |
| Found: | 54.4 | 8.1 | 20.5 | 17.0 |

(2) 2-(1-ethyl-n-propyl)-4,4-dimethyl-5-dimethylcarbamoyloxypyrazolin-(3)-one

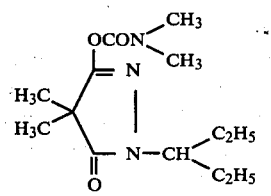

The pyrazolinedione salt is prepared from dimethyl dimethylmalonate and (1-ethyl-n-propyl)-hydrazine in a similar manner to that described in Example 1.

Further reaction to the carbamate takes place in absolute ether with dimethylcarbamoyl chloride, again in a similar manner to that described in Example 1.

Upon completion of the reaction the mixture is washed directly with water, sodium bicarbonate solution and again with water, and the ether is then dried and concentrated. The product is obtained in solid form and is briefly triturated with n-hexane, suction filtered and dried to improve crystallization.

Melting point: 73°–76° C.; yield: 65–75%.

|  | C | H | N | O |
|---|---|---|---|---|
| Calc.: | 58.0 | 8.6 | 15.6 | 17.8 |
| Found: | 57.5 | 9.1 | 15.4 | 18.0 |

(3) 2-phenyl-4,4-dimethyl-5-methyl-5-methoxycarbamoyloxypyrazolin-(3)-one

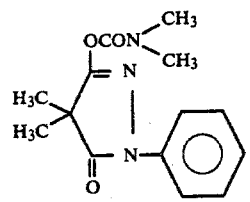

The starting materials are dimethyl dimethylmalonate and phenylhydrazine. The reaction and working up are analogous to those described in Example 1. The solid substance obtained after reaction with N-methyl- N-methoxycarbamoyl chloride in absolute acetonitrile and after working up as in Example 1 is triturated with n-hexane, suction filtered and dried at 40° C. at subatmospheric pressure.

Melting point: 48°–52° C.; yield: 60–80%.

|  | C | H | N |
|---|---|---|---|
| Calc.: | 57.7 | 5.9 | 14.4 |
| Found: | 53.2 | 6.0 | 14.2 |

The following compounds are obtained analogously:

| No. | $R^1$ | $R^2$ | $R^3$ | $R^4$ | $n_D^{25}$ m.p. |
|---|---|---|---|---|---|
| 4 | $CH_3$ | $CH_3$ | $-CH(CH_3)(C_3H_7)$ | $CH_3$ | 1.4662 |
| 5 | $CH_3$ | $CH_3$ | $-CH(CH_3)(C_2H_5)$ | $CH_3$ | 54°–62° C. |
| 6 | $CH_3$ | $CH_3$ | $-CH(CH_3)(CH_3)$ | $CH_3$ | 75°–80° C. |
| 7 | $CH_3$ | $CH_3$ | phenyl | $CH_3$ | 130°–132° C. |
| 8 | $CH_3$ | $CH_3$ | $CH_3$ | $CH_3$ | 95°–96° C. |
| 9 | $CH_3$ | $n\text{-}C_3H_7$ | $-CH(CH_3)(CH_3)$ | $CH_3$ | 1.4669 |
| 10 | $CH_3$ | $n\text{-}C_3H_7$ | $-CH(CH_2-CH_3)(CH_2-CH_3)$ | $CH_3$ | 1.4633 |
| 11 | $CH_3$ | $n\text{-}C_3H_7$ | $-CH(CH_3)(C_3H_7)$ | $CH_3$ | 1.4678 |
| 12 | $CH_3$ | $3\text{-}C_3H_7$ | phenyl | $CH_3$ | 1.5365 |
| 13 | $CH_3$ | $CH_3$ | $i\text{-}C_3H_7$ | $-OCH_3$ | 1.4614 |
| 14 | $CH_3$ | $n\text{-}C_3H_7$ | $i\text{-}C_3H_7$ | $-OCH_3$ | 1.4627 |
| 15 | $CH_3$ | $n\text{-}C_3H_7$ | phenyl | $OCH_3$ | 1.5278 |
| 16 | $CH_3$ | $n\text{-}C_4H_9$ | $CH_3$ | $CH_3$ | 1.4749 |
| 17 | $CH_3$ | $n\text{-}C_4H_9$ | $i\text{-}C_3H_7$ | $CH_3$ | 1.4690 |
| 18 | $C_2H_5$ | $C_2H_5$ | $CH_3$ | $CH_3$ | 1.4761 |
| 19 | $C_2H_5$ | $C_2H_5$ | $i\text{-}C_3H_7$ | $CH_3$ | 1.4663 |
| 20 | $CH_3$ | phenyl | $CH_3$ | $CH_3$ | 1.5379 |
| 21 | $CH_3$ | phenyl | $i\text{-}C_3H_7$ | $CH_3$ | 57°–59° C. |
| 22 | $CH_3$ | $n\text{-}C_3H_7$ | cyclohexyl | $CH_3$ | 1.4873 |

-continued

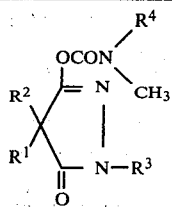

| No. | R¹ | R² | R³ | R⁴ | $n_D^{25}$ m.p. |
|-----|-----|-----|-----|-----|-----|
| 23 | CH₃ | CH₃ | —⟨H⟩ (cyclohexyl) | CH₃ | 101°–103° C. |
| 24 | CH₃ | n-C₃H₇ | —⟨H⟩ (cyclohexyl) | CH₃ | $n_D^{20} = 1.4890$ |
| 25 | CH₃ | n-C₃H₇ | —CH(CH₃)—CH₂—⟨phenyl⟩ | CH₃ | $n_D^{25} = 1.5150$ |
| 26 | CH₃ | n-C₃H₇ | —CH(CH₃)—⟨phenyl⟩ | CH₃ | 1.5143 |
| 27 | CH₃ | n-C₃H₇ | —CH₂—C(CH₃)₃ | CH₃ | 60°–62° C. |
| 28 | CH₃ | CH₃ | —⟨H⟩ (cyclohexyl) | CH₃ | 80°–87° C. |
| 29 | CH₃ | CH₃ | —CH(CH₃)—CH₂—⟨phenyl⟩ | CH₃ | 50°–51° C. |
| 30 | CH₃ | CH₃ | —CH(CH₃)—⟨phenyl⟩ | CH₃ | 1.5211 |
| 31 | CH₃ | CH₃ | —CH₂—C(CH₃)₃ | CH₃ | 1.4653 |
| 32 | CH₃ | C₂H₅ | CH₃ | CH₃ | 1.4802 |
| 33 | CH₃ | CH₃ | —⟨phenyl⟩ | CH₃ | 1.5418 |
| 34 | CH₃ | CH₃ | i-C₃H₇ | CH₃ | 46°–50° C. |
| 35 | (cyclohexyl) | | CH₃ | CH₃ | 69°–72° C. |
| 36 | (cyclohexyl) | | i-C₃H₇ | CH₃ | |

The active ingredient according to the invention may be used for combatting pests such as sucking and biting insects, Diptera and mites. It is possible to treat either the pests or the objects to be protected against pest attack with an effective amount of one or more of the active ingredients according to the invention.

The main representatives of the sucking insects are aphids (Aphidae) such as *Myzus persicae, Doralis fabae, Rhopalosiphum padi., Macrosiphum pisi, Macrosiphum solanifolii, Cryptomyzus korschelti, Sapaphis mali, Hyalopterus arundinis* and *Myzus cerasi,* and bugs such as *Piesma quadratum, Dysdercus intermedius, Cimex lectularius, Rhodnius prolixus* and *Triatoma infestans.*

The most important of the biting insects are Lepidoptera such as *Plutella maculipennis, Lymantria dispar., Euproctis chrysorrhoea* and *Malacosoma neustria,* further *Mamestra brassicae, Agrotis segetum, Pieris brassicae, Hyponomeuta padella, Ephestia kuhniella* and *Galleria mellonella.*

Other representatives of biting insects are beetles (Coleoptera) such as *Sitophilus granarius, Leptinotarsa decemlineata, Dermestes frischi, Tribolium castaneum,* Calandra or *Sitophilus zeamais, Stegobium paniceum, Tenebrio molitor,* including soil-borne species such as wireworms (*Agriotes spec.*) and cockchafers (*Melolontha melolontha*); cockroaches such as *Blatella germanica, Periplaneta americana, Blatta orientalis, Blaberus giganteus, Blaberus fusous,* and *Henschoutedenia flexivitta;* Orthoptera, e.g., *Acheta domestica,* termites such as *Reticulitermes flavipes,* and Hymenoptera such as ants, e.g., *Lasius niger.*

The Diptera essentially encompass flies such as *Drosophila melanogaster, Ceratitis capitata, Musca domestica, Fannia cancicularis, Phormia regina, Calliphora erythrocephala* and *Stomoxys calcitrans;* mosquitoes such as *Aedes aegypti, Culex pipiens* and *Anopheles stephensi.*

Of the mites (Acari) particular importance attaches to spider mites (Tetranychidae) such as *Tetranychus telaris* (=*Tetranychus althaeae* or *Tetranychus urticae*) and *Paratetranychus pilosus* (=*Panonychus ulmi*); gall mites, e.g., *Eriophyes ribis,* and Tarsonemidae, e.g., *Hemitarsonemus latus* and *Tarsonemus pallidus;* and finally ticks such as *Ornithodorus moubata.*

Particularly striking is the strong action on sucking insects, especially aphids such as *Aphis fabae, Aphis pomi, Aphis sambuci, Aphidula nasturtii, Coro apha gossypii, Sappaphis mali, Sappahis mala, Dysaphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acrythosi-*

*phon onobrychis, Macrosiphon rosae, Megoura viciae, Schizoneura lanuginosa, Eriosoma lanigerum, Pemphigus bursarius, Dreyfusia nordmannianae, Dreyfusia piceae, Adelges laricis,* and *Phyllocera vitifolii.*

Application of the active ingredients may be effected for instance in the form of directly sprayable solutions, powders, suspensions, dispersions, emulsions, oil dispersions, pastes, dusts, broadcasting agents, or granules by spraying atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

The amount of active ingredient in the ready-to-use liquors may vary within a wide range; it is generally from 0.0001 and 10%, preferably from 0.01 to 1%.

The active ingredients may also be successfully used in the ultra-low volume method, where it is possible to apply formulations containing up to 95% of active ingredient, or even the 100% active ingredient.

An example of a possible formulation is given below:

400 g of 2-methyl-4-methyl-4-n-propyl-5-dimethylcarbamoyloxypyrazolin-(3)-one
20 g of calcium dodecylbenzene sulfonate
80 g of alkoxylated fatty acid amide xylene makeup to 1,000 ml.

There may be added to the individual active ingredients or mixtures thereof (if desired, immediately before use (tankmix)) oils of various types, herbicides, fungicides, insecticides and bactericides.

Examples of active ingredients which may be admixed are as follows:

1,2-dibromo-3-chloropropane
1,3-dichloropropene
1,3-dichloropropene + 1,2-dichloropropane
1,2-dibromoethane
2-sec-butylphenyl-N-methylcarbamate
o-chlorophenyl-N-methylcarbamate
3-isopropyl-5-methylphenyl-N-methylcarbamate
o-isopropoxyphenyl-N-methylcarbamate
3,5-dimethyl-4-methylmercaptophenyl-N-methylcarbamate
4-dimethylamino-3,5-xylyl-N-methylcarbamate
2-(1,3-dioxolan-2-yl)-phenyl-N-methylcarbamate
1-naphthyl-N-methylcarbamate
2,3-dihydro-2,2-dimethylbenzofuran-7-yl-N-methylcarbamate
2,2-dimethyl-1,3-benzodioxol-4-yl-N-methylcarbamate
2-dimethylamino-5,6-dimethyl-4-pyrimidinyldimethylcarbamate
2-methyl-2-(methylthio)-propionaldehyde-O-(methylcarbamoyl)-oxime
S-methyl-N-[(methylcarbamoyl)-oxy]-thioacetimidate
methyl-N',N'-dimethyl-N-[(methylcarbamoyl)-oxy]-1-thiooxamidate
N-(2-methyl-4-chlorophenyl)-N',N'-dimethylformamidine
tetrachlorothiophene
O,O-dimethyl-O-(p-nitrophenyl)-phosphorothioate
O,O-diethyl-O-(p-nitrophenyl)-phosphorothioate
O-ethyl-O-(p-nitrophenyl)-phenylphosphonothioate
O,O-dimethyl-O-(3-methyl-4-nitrophenyl)-phosphorothioate
O,O-diethyl-O-(2,4-dichlorophenyl)-phosphorothioate
O-ethyl-O-(2,4-dichlorophenyl)-phenylphosphonothioate
O,O-dimethyl-O-(2,4-trichlorophenyl)-phosphorothioate
O-ethyl-O-(2,4,5-trichlorophenyl)-ethyl-phosphonothioate
O,O-dimethyl-O-(4-bromo-2,5-dichlorophenyl)-phosphorothioate O,O-dimethyl-O-(2,5-dichloro-4-iodophenyl)-phosphorothioate
O,O-dimethyl-O-(3-methyl-4-methylthiophenyl)-phosphorothioate
O-ethyl-O-(3-methyl-4-methylthiophenyl)-isopropyl-phosphoramidate
O,O-diethyl-O-[p-(methylsulfynyl)-phenyl]-phosphorothioate
O-ethyl-S-phenylethylphosphonodithioate
O,O-diethyl-[2-chloro-1-(2,4-dichlorophenyl)-vinyl]-phosphate
O,O-dimethyl-[2-chloro-1-(2,4,5-trichlorophenyl)]-vinylphosphate
O,O-dimethyl-S-(1-phenyl)-ethylacetate phosphorodithioate
bis-(dimethylamino)-fluorophosphine oxide
octamethyl-pyrophosphoramide
O,O,O,O-tetraethyldithiopyrophosphate
S-chloromethyl-O,O-diethylphosphorodithioate
O-ethyl-S,S-dipropylphosphorodithioate
O,O-dimethyl-O-2,2-dichlorovinylphosphate
O,O-dimethyl-1,2-dibromo-2,2-dichloroethylphosphate
O,O-dimethyl-2,2,2-trichloro-1-hydroxyethylphosphonate
O,O-dimethyl-S-[1,2-biscarbethoxyethyl-(1)]-phosphorodithioate
O,O-dimethyl-O-(1-methyl-2-carbomethoxyvinyl)-phosphate
O,O-dimethyl-S-(N-methylcarbamoylmethyl)-phosphorodithioate
O,O-dimethyl-S-(N-methylcarbamoylmethyl)-phosphorothioate
O,O-dimethyl-S(N-methoxyethylcarbamoylmethyl)-phosphorodithioate
O,O-dimethyl-S-(N-formyl-N-methylcarbamoylmethyl)-phosphorodithioate
O,O-dimethyl-O-[1-methyl-2-(methylcarbamoyl)-vinyl]-phosphate
O,O-dimethyl-O-[(1-methyl-2-dimethylcarbamoyl)-vinyl]-phosphate
O,O-dimethyl-O-[(1-methyl-2-chloro-2-diethylcarbamoyl)-vinyl)]phosphate
O,O-diethyl-S-(ethylthiomethyl)-phosphorodithioate
O,O-diethyl-S-[(p-chlorophenylthio)-methyl]-phosphorodithioate
O,O-dimethyl-S-(2-ethylthioethyl)-phosphorothioate
O,O-dimethyl-S-(2-ethylthioethyl)-phosphorodithioate
O,O-dimethyl-S-(2-ethylsulfynylethyl)-phosphorothioate
O,O-diethyl-S-(2-ethylthioethyl)-phosphorodithioate
O,O-dimethyl-S-(2-ethylsulfynylethyl)-phosphorothioate
O,O-diethylthiophosphoryliminophenylacetonitrile
O,O-diethyl-S-(2-chloro-1-phthalimidoethyl)-phosphorodithioate
O,O-diethyl-S-[6-chlorobenzoxazolon-(2)-yl-(3)]-methyldithiophosphate
O,O-dimethyl-S-[2-methoxy-1,3,4-thiodiazol-5-onyl-(4)-methyl]-phosphorodithioate
O,O-diethyl-O-[3,5,6-trichloropyridyl-(2)]-phosphorothionate
O,O-diethyl-O-(2-pyrazinyl)-phosphorothioate
O,O-diethyl-O-[2-isopropyl-4-methylpyrimidinyl-(6)]-phosphorothioate
O,O-diethyl-O-[2-(diethylamino)-6-methyl-4-pyrimidinyl]-thionophosphate
O,O-dimethyl-S-(4-oxo-1,2,3-benzotriazin-3-ylmethyl)-phosphorodithioate
O,O-dimethyl-S-[(4,6-diamino-1,3,5-triazin-2-yl)-methyl]-phosphorodithioate
O,O-diethyl-(1-phenyl-1,2,4-triazol-3-yl)-thionophosphate
O,S-dimethylphosphoramidothioate
O,S-dimethyl-N-acetylphosphoramidothioate
hexachlorocyclohexane
1,1-di-(p-methoxyphenyl)-2,2,2-trichloroethane
6,7,8,9,10,10-hexachloro-1,5,5a,6,9,9a-hexahydro-6,9-methano-2,4,3-benzodioxathiepine-3-oxide These agents may be added to the compounds according to the invention in a ratio by weight of from 1:10 to 10:1.

The following examples demonstrate the biological action. The agent used for comparison purposes is 1-naphthyl-N-methylcarbamate (German 1,138,277).

EXAMPLE 1

Contact action on aphids (*Aphis fabae*), spray experiment

Potted bean plants (*Vicia faba*) heavily infected with aphid colonies are sprayed to runoff in a spray chamber with aqueous formulations containing various active ingredient concentrations.

The kill rate is determined after 24 hours.

| Compound no. | Concentration of active ingredient in formulation (%) | Kill rate (%) |
| --- | --- | --- |
| 1 | 0.001 | 100 |
| 2 | 0.01 | 100 |
|  | 0.005 | 80 |
| 4 | 0.02 | 80 |
| 6 | 0.005 | 100 |
| 8 | 0.02 | 100 |
| 9 | 0.005 | 80 |
| 11 | 0.01 | 100 |
| 17 | 0.001 | 95 |
| 18 | 0.001 | 90 |
| 19 | 0.01 | 80 |
| 20 | 0.0025 | 100 |
| Comparative agent | 0.04 | 100 |
|  | 0.02 | 50 |

EXAMPLE 2

Systemic action of aphids (*Aphis fabae*); watering experiment

The soil around heavily aphid-infected bean plants in plastic pots (8 cm in diameter) filled with 300 g of compost is watered with 20 ml of aqueous formulations containing various active ingredient concentrations.

The kill rate is determined after 48 hours.

| Compound no. | Concentration of active ingredient in formulation (%) | Kill rate (%) |
| --- | --- | --- |
| 1 | 0.001 | 100 |
| 2 | 0.1 | 100 |
| 4 | 0.05 | 100 |
| 6 | 0.005 | 80 |
| 8 | 0.01 | 80 |
| 9 | 0.025 | 100 |
| 10 | 0.1 | 100 |
| 11 | 0.025 | 100 |
| 17 | 0.005 | 100 |
| 18 | 0.001 | 90 |
| 20 | 0.05 | 80 |
| Comparative |  |  |

-continued

| Compound no. | Concentration of active ingredient in formulation (%) | Kill rate (%) |
|---|---|---|
| agent | 0.1 | ineffective |

EXAMPLE 3

Continuous contact action on houseflies (*Musca domestica*)

Both covers and bottoms of Petri dishes 10 cm in diameter are lined with a total of 2 ml of acetonic solutions containing various active ingredient concentrations. After evaporation of the solvent (about 30 minutes), 10 flies are introduced into each dish. The kill rate is determined after 4 hours.

| Compound no. | Amount of active ingredient per dish (mg) | Kill rate (%) |
|---|---|---|
| 4 | 0.2 | 100 |
| 6 | 0.02 | 100 |
| 8 | 0.2 | 100 |
| 9 | 0.01 | 80 |
| 10 | 0.2 | 80 |
| 11 | 0.2 | 100 |
| 17 | 0.2 | 100 |
| 18 | 0.2 | 80 |
| 19 | 0.02 | 100 |
| Comparative agent | 1.0 | 100 |
|  | 0.5 | 60 |

EXAMPLE 4

Contact action on ticks (*Ornithodorus moubata*)

Young ticks having a diameter of from 1.5 to 2 mm are placed in gauze bags and dipped for 5 seconds in test emulsions of various concentrations. The kill rate is determined after 48 hours.

| Compound no. | Concentration of test emulsion (%) | Kill rate (%) |
|---|---|---|
| 1 | 0.04 | 100 |
| 4 | 0.1 | 100 |
| 8 | 0.04 | 100 |
| 9 | 0.1 | 100 |
| 17 | 0.005 | 100 |
| 18 | 0.01 | 80 |

We claim:

1. A carbamate of the formula

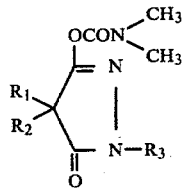

where $R_1$ and $R_2$ are identical or different and each is linear or branched alkyl of 1 to 4 carbon atoms or phenyl, and $R_3$ is linear or branched alkyl of 1 to 6 carbon atoms which is optionally substituted by phenyl or methoxy or is cycloalkyl of 3 to 6 carbon atoms, unsubstituted phenyl or phenyl bearing one or more halogen substituents.

2. 1-methyl-4-methyl-4-n-propyl-3-dimethylcarbamoyloxy-pyrazolin-(5)-one.

3. A composition for combatting pests, comprising an effective amount of the carbamate set form in claim 1 and one or more suitable carriers.

4. A process for combatting pests, wherein the pests or the objects to be protected against pest attack are treated with an effective amount of a carbamate as claimed in claim 1.

* * * * *